(12) United States Patent
Shavelson

(10) Patent No.: US 7,938,788 B2
(45) Date of Patent: May 10, 2011

(54) FOOT TYPING METHOD

(76) Inventor: Dennis Shavelson, Suffern, NY (US)

( * ) Notice: Subject to any disclaimer, the term of this patent is extended or adjusted under 35 U.S.C. 154(b) by 654 days.

(21) Appl. No.: 11/619,854

(22) Filed: Jan. 4, 2007

(65) Prior Publication Data

US 2008/0167582 A1    Jul. 10, 2008

(51) Int. Cl.
*A61B 5/103* (2006.01)
(52) U.S. Cl. .......................... 600/592; 33/515
(58) Field of Classification Search .................. 600/592; 33/515; 36/140
See application file for complete search history.

(56) References Cited

U.S. PATENT DOCUMENTS

| | | | | |
|---|---|---|---|---|
| 4,868,945 A | * | 9/1989 | DeBettignies | 12/142 N |
| 4,917,105 A | * | 4/1990 | Tiitola et al. | 600/592 |
| 6,141,889 A | * | 11/2000 | Baum | 36/140 |
| 6,170,177 B1 | * | 1/2001 | Frappier et al. | 12/142 R |
| 7,069,665 B1 | * | 7/2006 | Adriano | 33/515 |
| 2001/0000369 A1 | * | 4/2001 | Snyder et al. | 36/44 |
| 2006/0213090 A1 | * | 9/2006 | Nole | 36/140 |

OTHER PUBLICATIONS

Palmer. "Fundamentals of Musculoskeletal techniques" Ch 14 Ankle and Foot. pp. 365-372.*
Paul Scherer and Jack Morris, "The Classification of human foot types, abnormal foot function, and pathology" in Clinical Biomechanics of the Lower Extremities, Chapter 3, pp. 85-93, (Valmassey, Ronald L. ed., 1996).

* cited by examiner

*Primary Examiner* — Max Hindenburg
*Assistant Examiner* — Renee Danega
(74) *Attorney, Agent, or Firm* — Norris McLaughlin & Marcus, P.A.

(57) ABSTRACT

A method for classifying foot types by measuring the position of the Rearfoot Supinatory End Range of Motion, the Rearfoot Pronatory End Range of Motion, the Forefoot Supinatory End Range of Motion and the Forefoot Pronatory End Range of Motion, and classifying the foot based on the results of these measurements is disclosed. Once a human foot is classified and typed according to the disclosed method, a treatment plan can be customized for the specific foot type. The treatment can include the use of pre-orthotic pads and orthotic inserts which are customized according to a patient's specific foot type.

8 Claims, 3 Drawing Sheets

FOOT TYPING METHOD

FIELD OF THE INVENTION

The present invention relates to a novel method for profiling feet in order to classify feet into one of sixteen functional foot types in a human patient. A further embodiment of the present invention relates to the diagnosis and treatment of pedal and postural conditions based on a human patient's functional foot type. An even further embodiment relates to novel pre-orthotic foot pads and orthotic devices constructed according to a patient's functional foot type.

BACKGROUND OF THE INVENTION

The human foot contains twenty-six bones, each having a unique size and shape. The foot can be divided into three main sections, the rearfoot, forefoot and digits (toes). The rearfoot consists of the Talus and the Calcaneus bones, and forms the shorter pillar of the longitudinal arches of the foot. The Forefoot consists of the Navicular, the Cuboid, the three Cuneiforms and the five Metatarsals and forms the longer pillar of the longitudinal arches of the foot. The digits comprise the great toe, or Hallux, which comprises two Phalanges, and the $2^{nd}$, $3^{rd}$, $4^{th}$ and $5^{th}$ toes which comprise three Phalanges. The digits are involved in adaptation and fine movement but are not very important in the stability and function of the foot and posture.

The foot also contains thirty-three joints. Each joint connects the ends of two bones and they allow those bones to move on one or more of the body planes within certain ranges of motion. The foot also contains over one hundred muscles, tendons and ligaments which provide leverage, mobility and stability as they expand and contract. The muscles, tendons and ligaments can move the rearfoot and forefoot as flexible units or they can keep them in a strong arched position. This means that and they can allow the both pillars to be very rigid and supportive or very flexible or adaptive or any combination of the two at different times and under different circumstances.

The human foot can differ substantially when comparing the feet of individuals. Even a single individual can have significant differences between their right and left feet. These massive and diverse differences can produce a seemingly infinite number of possibilities when trying to classify and categorize human feet into groups in order to aid in the diagnosis and treatment of various pedal and postural conditions and diseases. Accordingly, some of the most basic questions in foot care remain unanswered: Why do certain feet develop abnormalities while others do not? Why are foot and postural problems inherited? Why does a treatment regimen work for certain feet, but fail in others? Why do certain feet develop deformity, degeneration and pain while others do not? Why are certain feet skilled for one function yet other feet have difficulty performing the same function? The foregoing questions lead to the study and classification of feet into types in order to assist in the diagnosis and treatment of pedal and postural conditions.

Early prior art methods for classifying foot types grouped feet according to specific characteristics, namely the three medical arch types: low, normal and high. Other types of feet have been described as the "Greek Foot", "The Morton's Foot" and the "French" or "Peasants Foot". These simple classification systems continue to be used by practitioners to diagnose and treat conditions, as well as to facilitate the fabrication of shoe lasts, insoles and orthotics.

More recently, the "Root" theory focuses on Subtalar joint (rearfoot) control in order to improve ground reactive support in feet to prevent degeneration and deformity and classifies unhealthy feet by pathology such as compensated subtalar varus or uncompensated forefoot Valgus. Most of the advances in function lower extremity biomechanics during the last three decades are based on "Root" theory, and focus on Subtalar joint range of motion and deviations from Subtalar neutral position in order to diagnose and treat a human foot. Howe Accordingly, the prior art methods for classifying feet are limited in their scope and often fail to properly and accurately classify all feet. Therefore, there is a need for a method of profiling feet into a uniform system that classifies and types every possible foot, and to use the specific foot type to diagnose and treat various pedal and/or postural conditions in order to improve outcomes, reduce failures and allow practitioners to offer care when it comes to prevention and performance issues.

SUMMARY OF THE INVENTION

The present invention is directed to a method for classifying a human foot into a distinct foot type based on positional measurements in the Rearfoot and Forefoot of a foot. The Rearfoot positional measurements include the Rearfoot Supinatory End Range of Motion and the Rearfoot Pronatory End Range of Motion, while the Forefoot positional measurements include the Forefoot Supinatory End Range of Motion and the Forefoot Pronatory End Range of Motion. Once a practitioner determines these measurements based on the present invention, every foot can be classified into a specific foot type. A Rearfoot type is determined according to the two Rearfoot measurements, and, a Forefoot type is determined according to the two Forefoot measurements. Together, the Rearfoot and Forefoot measurements comprise a Functional Foot Type according to an embodiment of the present invention.

Another aspect of the present invention involves the treatment of pedal and postural conditions based on patients' Functional Foot Types. Because certain conditions can be predicted and diagnosed based on an individuals Functional Foot Type, treatments including pre-orthotic foot pads and orthotic inserts can be customized based on the Functional Foot Type. Accordingly, the present invention also includes Functional Foot Type-specific pre-orthotic pads, and orthotic inserts that are casted and/or posted according to Functional Foot Type-specific guidelines.

DETAILED DESCRIPTION OF THE INVENTION

Figure 1:
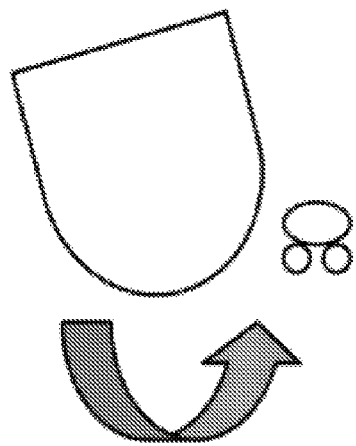
FIG. 1 is an illustration of a Rearfoot Subtalar End Range of Motion ("SERM") in an invented position

A fundamental basis of the present invention is premised in the understanding that the human foot contains three distinct dynamic arches, the medial longitudinal arch, the lateral longitudinal arch and the transverse midfoot arch. When discussing the anatomy of human feet certain bony prominences that, when weighted, touch the ground surface and give every foot the potential to lock into a supportive arched configuration needed to insure a lifetime of healthy performance. According to the present invention, these foundational surfaces are known as pillars. The hollow that is created on the plantar surface of the foot by the bones of the three dynamic arches that are not touching the ground surface is known as the Vault of the foot.

When defining the Vault longitudinally from heel to toe, the Talus bone can be viewed as the "keystone" of both the lateral longitudinal arch and the medial longitudinal arch, but is centered in neither. The medial longitudinal arch is located on the outside of the big toe side of the foot and has two pillars. The posterior pillar is the short pillar, and contains only one bone, the Calcaneous. The anterior pillar of the medial arch contains six bones, the Navicular, the medical medial Cuneiform, the intermediate Cuneiform, and the first, second and third Metatarsals.

The lateral longitudinal arch is located on the outside of the smallest toe, and similarly has posterior and anterior pillars. The posterior pillar of the lateral arch is the shorter of the two, and is comprised of the Talus and the posterior two-thirds of the Calcaneus. The anterior pillar is comprised of the anterior one-third of the Calcaneous, the Cuboid and the fourth and fifth Metatarsals.

The transverse midfoot arch, located transversally at the level of Midfoot, is represented by the Cuneiforms and the Cuboid. The Middle Cuneiform is the "keystone" of this arch, and is not centered.

In each of these arches and the joints that comprise the arch, tendons, ligaments and soft tissue capsules provide support, leverage and flexibility in varied proportions depending on the specific task. If any of the three arches fail to deliver the necessary combination of support and flexibility needed for various tasks such as stance, gait, side to side movement and sports function, conditions including deformity, pain and overuse syndromes of the foot and postural breakdown of the foot can occur.

When examining a human foot as a whole from heel to toe, the midtarsal joint can be viewed as a keystone joint of one large arch. It separates the foot into two distinct segments or pillars, the Rearfoot, located proximal (behind) to the Midtarsal joint, and the Forefoot, located distal (forward) to the Midtarsal joint.

The three dynamic arches of the foot must have the ability to adapt to different foundational surfaces and further to assist in functions such as seated support, standing support and walking or running. Ideally, the dynamic arches of the foot change from a rigid lever (support) into a functional adaptor (movement) at precisely the right moment as we stand, walk or exercise so as not to create degeneration, deformity or overuse in the feet and posture.

In reality, when it comes to profiling feet, some feet are excellent rigid levers and some feet are excellent functional adaptors and many lie in between these two extremes. More specifically, some feet have a Rearfoot that is an excellent rigid lever and some feet have a Rearfoot that is an excellent functional adaptor and many lie in between these two extremes. In addition, some feet have a Forefoot that is an excellent rigid lever and some feet have a Forefoot that is an excellent functional adaptor and many lie in between these two extremes. It is theorized that every functional foot type, for one reason or another, is flawed either as a rigid lever or a functional adaptor, or both, especially when impacted by additional factors such as a body weight, activity level, body type and health state. This pathology, unless compensated, predicts a foot type specific set of deformities, degenerative changes, overuse syndromes and quality of life issues. Once profiled and diagnosed for foot type according to one embodiment of the present invention, functional foot type specific treatment can be introduced in order to prevent, eliminate or reduce these problems from downgrading our quality of life over time.

Accordingly, one embodiment of the present invention relates to a foot typing method based upon two positional measurements of the Rearfoot, and two positional measurements of the Forefoot. The two rear foot measurements include the Rearfoot Supinatory End Range of Motion position, or "Rearfoot SERM", and the Rearfoot Pronatory End Range of Motion position, or "Rearfoot PERM". The two forefoot measurements are the Forefoot Supinatory End Range of Motion position or "Forefoot SERM", and the Forefoot Pronatory End Range of Motion position, or "Forefoot PERM".

The Rearfoot SERM position refers to the position the Rearfoot Joint assumes in open chain, i.e., when not weighted on the ground, with reference to a bisection of the lower one third of the leg after applying a strong inversion force upon the Calcaneus until it can no longer move. This is performed by inverting the foot so that it can no longer move, followed by determining whether the position is inverted or everted. If the Rearfoot Joint is tilted toward the medial arch, the Rearfoot SERM position is inverted. If the Rearfoot Joint is tilted toward the lateral arch, the Rearfoot SERM position is everted The Rearfoot PERM position refers to the position that the Subtalar Joint assumes in open chain with reference to a bisection of the lower one third of the leg after applying a strong eversion force upon the Calcaneous until it can no longer move. This is done by everting the foot until it can no longer move, followed by determining whether the position is inverted, vertical or everted. If the Subtalar Joint is tilted toward the medial column, the Rearfoot PERM position is inverted. If the Subtalar Joint is vertical to the ground, the Rearfoot PERM is perpendicular. And if the Subtalar Joint is tilted toward the medial arch, the Rearfoot PERM position is everted.

The Forefoot SERM position is the position the first metatarsal assumes in open chain with reference to the fifth metatarsal after applying a strong plantarflectory force downward upon the first metatarsal from above until it can no longer move. The lateral arch is stabilized and a downward force is applied upon the first metatarsal head from above until the first metatarsal cannot move any further in the downward direction. If the first metatarsal is positioned above the fifth metatarsal, the position is dorsiflexed. If the first metatarsal is positioned below the fifth metatarsal, the position is plantarflexed.

The Forefoot PERM position is the position the first metatarsal assumes in open chain with reference to the fifth metatarsal after applying a strong dorsiflectory force upward upon the first metatarsal from below until it can no longer move. If the first metatarsal is positioned above the fifth metatarsal, the position is dorsiflexed. If the first metatarsal is positioned level to the first metatarsal, the position is vertical. And if the first metatarsal is positioned below the fifth metatarsal, the position is plantarflexed.

After making the four diagnostic measurements, the recorded positions allow every foot to be classified into one of four Rearfoot types known as rigid, stable, flexible or flat, and one of four Forefoot types known as rigid, stable, flexible or flat.

Figure 2:
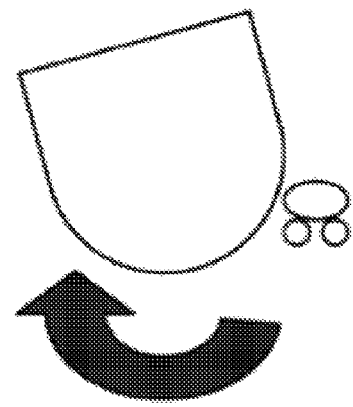
FIG. 2 is an illustration of a Rearfoot Pronatory End Range of Motion ("PERM") in an invented position
Figure 3:
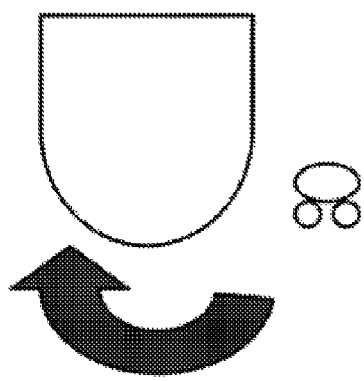
FIG. 3 is an illustration of a Rearfoot PERM in a perpendicular position
Figure 4:
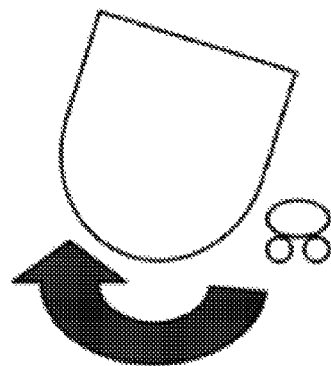
FIG. 4 is an illustration of a Rearfoot PERM in an everted position
Figure 5:
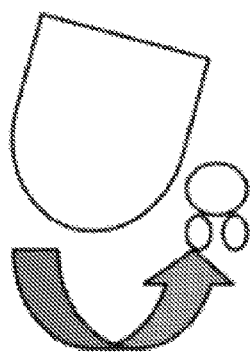
FIG. 5 is an illustration of a Rearfoot SERM in an everted position

The four Rearfoot types can be described as follows. A rigid rearfoot has an inverted Rearfoot SERM (FIG. 1) and an inverted Rearfoot PERM (FIG. 2). A stable rearfoot has an inverted Rearfoot SERM (FIG. 1) and a vertical Rearfoot PERM (FIG. 3). The flexible rearfoot has an inverted Rearfoot SERM (FIG. 1) and an everted Rearfoot PERM (FIG. 4). Finally, the flat rearfoot has an everted Rearfoot SERM (FIG. 5) and an everted Rearfoot PERM (FIG. 4).

Figure 6:
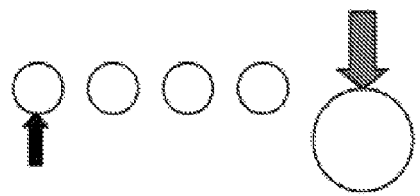
FIG. 6 is an illustration of a Forefoot SERM in a plantarflexed position
Figure 7:
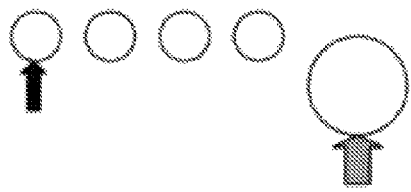
FIG. 7 is an illustration of a Forefoot PERM in a plantarflexed position
Figure 8:
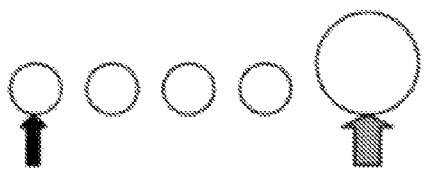
FIG. 8 is an illustration of a Forefoot PERM in a vertical position
Figure 9:
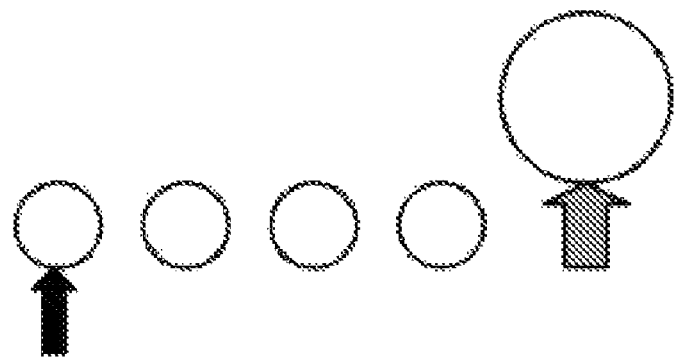
FIG. 9 is an illustration of a Forefoot PERM in a dorsiflexed position
Figure 10:
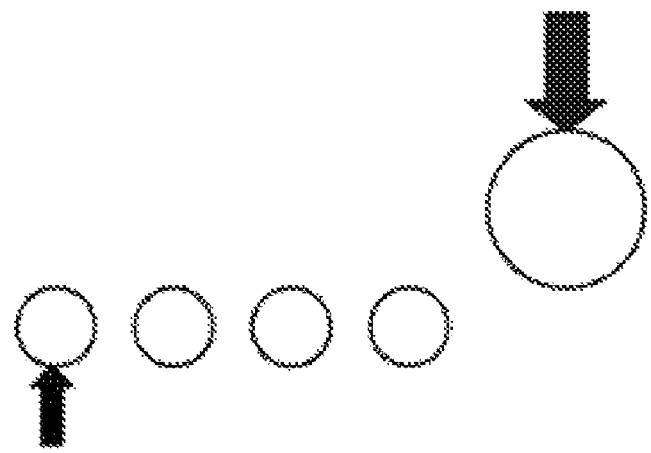
FIG. 10 is an illustration of a Forefoot SERM in a dorsiflexed position

The forefoot types are described in similar terms as the rearfoot, and are as follows. The rigid forefoot has a plantarflexed Forefoot SERM (FIG. 6) and a plantarflexed Forefoot PERM (FIG. 7). The stable forefoot has a plantarflexed Forefoot SERM (FIG. 6) and a vertical Forefoot PERM (FIG. 8). The flexible forefoot has a plantarflexed Forefoot SERM (FIG. 7) and a dorsiflexed Forefoot PERM (FIG. 9). Finally, the flat forefoot has a dorsiflexed Forefoot SERM (FIG. 10) and a dorsiflexed Forefoot PERM.

Accordingly, when the four Rearfoot types are plotted horizontally and the four Forefoot types are plotted vertically on a table, a matrix of 16 possible functional foot types are possible, as shown in Table 1.

TABLE 1

| | | Forefoot Type | | | |
|---|---|---|---|---|---|
| | | Rigid | Stable | Flexible | Flat |
| Rearfoot Type | Rigid | Rigid/Rigid | Rigid/Stable | Rigid/Flex | Rigid/Flat |
| | Stable | Stable/Rigid | Stable/Stable | Stable/Flex | Stable/Flat |
| | Flexible | Flex/Rigid | Flex/Stable | Flex/Flex | Flex/Flat |
| | Flat | Flat/Rigid | Flat/Stable | Flat/Flex | Flat/Flat |

Each Functional Foot Type of present invention is associated with a certain profile of features that define that functional foot type. These include open and closed chain presentation, forefoot lesion pattern, x-ray presentation, shoe wear pattern, foot deformities, foot pain and fatigue syndromes and postural pain, deformity and fatigue syndromes. Although more than one Functional Foot Type may share some characteristics, each Functional Foot Type has a profile of characteristics that are foot type specific. As a result, once a patient's foot has been typed and classified according to one embodiment of the present invention, a treatment plan that is foot type specific can be developed that has a higher level of success and a lower failure rate than utilizing previous systems. Functional Foot Type-specific treatment also enables practitioners to be more successful when it comes to prevention and performance issues.

The dynamic arches of the foot must be strong and supportive at certain times and functional and adaptive at others. This means that unlike an architectural arch, the dynamic arches of the foot, in order to perform, must sacrifice their ability to support in order to provide the flexibility and agility needed in order to stand, walk, work, etc. In the flexible and stable rearfoot and forefoot types it is the repetitive need for the foot to multitask over a lifetime and the inherent fact that the dynamic arches of the foot cannot become a rigid lever quickly enough after becoming flexible and adaptive when performing that creates pathology. One or more of the dynamic foot arches weaken and even collapse over time unless supported externally. In the rigid and flat rearfoot and forefoot types, it is the repetitive need for the foot to multitask over a lifetime and the inherent fact that the dynamic arches of the foot cannot become flexible and adaptive quickly enough after being stable that creates pathology. One or more of these arches need balancing to the ground and each other. Accordingly, a treatment plan according to the present invention is based on supporting and balancing the dynamic arches, wherein support is achieved through a technique called centring.

Centring of the foot is typically accomplished through the use of felt and foam pre-orthotic pads, and orthotic inserts. Pre-orthotic pads used in accordance with the present invention are called Functional Foot Type pads, and orthotic inserts used according to the present invention are called Functional Foot Type orthotics. Functional Foot Type pads are specific felt and foam pads that begin the centring process. They are placed onto a shoe insole, or directly into the shoe, in order to test for the effectiveness of a functional foot type orthotic for future use. Additionally, Functional Foot Type pads serve to buffer or dampen the foot and postural break-in that corrective orthotics force the body to endure. If Functional Foot Type pads provide a patient with pain and/or symptom relief, or improve gait and posture, then the patient should find increased and/or permanent advantages when using Functional Foot Type orthotics with less failure due to the body rejecting the break-in process. As such, Functional Foot Type pads are necessary but often temporary, and are replaced by an orthotic insert once the patient's custom Functional Foot Type orthotics are fabricated.

Functional Foot Type Treatment

The functional foot typing system of the present invention allows every foot, once typed to be treated foot type specific by creating a foot type specific custom centring device. Examples of centring devices for treatment include Functional Foot Type pads and Functional Foot Type orthotics.

Functional Foot Type Pads

Functional foot type pads are centring pads that are applied in one of three ways in order to begin the centring process. They can be applied to the inside of a shoe. They can be applied to a removable shoe insole that can then be moved from shoe to shoe or they can be applied to an existing foot orthotic in order to upgrade them as a centrum.

Functional Foot Type pads are applied foot type specific to the Rearfoot, medial longitudinal arch and the forefoot as follows:

(1)
Rigid Rearfoot Types: Apply pre-orthotic half heel pads to force the foot in Varus (inverted) position
Stable Rearfoot Types: No heel pad
Flexible Rearfoot Types: Apply pre-orthotic half heel pads in Varus
Flat Rearfoot Types: Apply pre-orthotic half heel pads in Valgus (everted) position
(2)
Apply pre-orthotic arch pads such that they sit underneath the highest point of the medial longitudinal arch to all Functional Foot Types
(3)
Rigid Forefoot Types: Apply the pre-orthotic wedged forefoot pad proximal to 2-5 Metatarsal heads in Valgus
Stable Forefoot Types: Apply the pre-orthotic wedged forefoot pad proximal to 2-5 Metatarsal heads in Varus Flexible Forefoot Types: Apply a pre-orthotic wedged forefoot pad proximal to 2-5 Metatarsal heads in Varus Flat Forefoot Types: Apply the pre-orthotic wedged forefoot pad proximal to 1-4 Metatarsal heads in Varus Functional Foot Type Orthotics Foot orthotics of the prior art generally are simple and non-patient specific in regards to postings and other modifications. They are only very slightly arched, are long, wide and the shell is poorly posted and modified. In summary, they lack centring. Functional Foot Type orthotics according to the present invention, on the other hand, are advanced foot orthotics that have a shell (body) that is fabricated from a negative plaster or fiberglass cast which is positive poured and to which custom postings and modifications are prescribed utilizing foot type specific techniques of the present invention. The resulting orthotics has a higher arch and is shorter and narrower than foot orthotics of the prior art. In summary, they provide the Vault of the foot with more centring. In addition, the accompanying prescription that is generated by the practitioner contains custom modifications, postings and corrections to balance the shell foot type and patient specific since there are variations within each foot type.

Since Functional Foot Type orthotics of the present invention improve longitudinal and transverse splay and spread, they are shorter and narrower than other known orthotics. Since they fill the Vault of the foot better than any other orthotics, Functional Foot Type orthotics are taller and have a higher arch. In addition, they correct for hammertoe influence. They are always posted in both the rearfoot and the forefoot and they contain foot type specific forefoot and rearfoot modifications.

Casting Techniques for Functional Foot Type Orthotics

When casting a patient for Functional Foot Type orthotics, techniques of the present invention have been developed that when utilized foot type specific, create an orthotic shell that provides better centring.

These casting techniques include:

1. Lateral Longitudinal Arch Correction. The practitioner places upward force under the fifth or fourth and fifth metatarsal heads stopping at a point when the rearfoot begins to be influenced.
2. Rearfoot Serm-Perm Balancing. The practitioner moves the cast from an inverted position to vertical under the lower one third of the leg eliminating the need for varus rearfoot posting.
3. Rearfoot Vault Enhancement. The practitioner grasps the back of the Calcaneus of the foot with the palm and the $2^{nd}$-$5^{th}$ fingers and then utilizing the thumb at the plantar surface of the Calcaneus exerts an upward force elevating the Calcaneus thereby expanding the rearfoot vault.
4. Forefoot Vault Enhancement. The practitioner exerts a downward force at the top of the first metatarsal head until end range of motion.
5. Hammertoe Correction. The practitioner places the second finger across the bases of the toes dorsally and exerts a downward force until the toes are seen to be on line with the metatarsal heads and not knuckled.

Accordingly, plaster or fiberglass casts are cast corrected according to the patient's specific Functional Foot Type, and Functional Foot Type orthotics of the present invention are constructed as follows:

(1)
Rigid Rearfoot Types: Utilize standard "Root" neutral casting technique.
Stable Rearfoot Types: Utilize Serm-Perm Balancing and Rearfoot vault enhancement techniques.
Flexible Rearfoot Types: Utilize Serm-Perm Balancing and Rearfoot vault enhancement techniques.
Flat Rearfoot Types: Utilize standard "Root" casting technique.

(2)
Apply the lateral longitudinal arch correction technique to all casts, regardless of functional foot type.

(3)
Rigid Forefoot Types: Utilize standard "Root" casting technique.
Stable Forefoot Types: Utilize Forefoot Vault Enhancement technique.
Flexible Forefoot Types: Utilize Forefoot Vault Enhancement technique.
Flat Forefoot Types: Utilize standard "Root" technique.

(4)
Utilize Hammertoe Correction technique for all casts, regardless of functional foot type.

Functional Foot Type Orthotic Prescription Guidelines

A foot type specific and custom prescription accompanies the corrected negative cast corrected models to the laboratory. Once the foot centring shell has been fabricated, the laboratory adds balancing materials (Posts) to the back and front of the shell by prescription. In addition, prescribed modifications to the plastic shell in the form of cutouts allow for additional centring to the vault of the foot, depending upon the specific foot type.

The prescribing techniques are as follows:
1. Rearfoot Posting. The use of angulated or vertical materials and lifts that balance the rearfoot to the weightbearing surface. Rearfoot posts can be Varus, flat (Vertical) or Valgus.
2. Forefoot Posting. The use of angulated or vertical materials that balance the forefoot to the weightbearing surface. Forefoot posts can be posts can be Varus, flat (Vertical) or Valgus.
3. Forefoot Ray Cutouts. Material is removed from the Functional Foot Type orthotic shell to allow specific metatarsals to drop, thus enhancing the centring of the forefoot vault by leveraging the muscles, tendons, ligaments and soft tissue.

Prescription guidelines are ordered foot type specific as follows:

Rigid Rearfoot Types: Utilize a Varus rearfoot post. Add additional lift to the rearfoot post as tolerable to the inside of the shoe to accommodate functional equinus.
Stable Rearfoot Types: Utilize a flat (Vertical) rearfoot post.
Flexible Rearfoot Types: Utilize a flat (Vertical) rearfoot post.
Flat Rearfoot Types: Utilize a Valgus rearfoot post.
Rigid Forefoot Types: Utilize a 1-4 Valgus forefoot post with a first ray cutout.
Stable Forefoot Types: Utilize a 2-5 Varus forefoot post with a first ray cutout.
Flexible Forefoot Types: Utilize a 2-5 Varus forefoot post with a first ray cutout.
Flat Forefoot Types: Utilize a 1-5 Varus forefoot post.

EXAMPLES

Example 1

During examination, a patient's Rearfoot and Forefoot measurements are taken according to the present invention. The patient shows a Rearfoot SERM position as inverted, a Rearfoot PERM position as Inverted, a Forefoot SERM as Planarflexed and a Forefoot PERM as Dorsiflexed. Accordingly, the patient's functional foot type is Rearfoot Rigid/Forefoot Flexible. Functional Foot Type Pads are then applied to the patient's shoes according to the guidelines for the specific functional foot type, and are as follows: (1) Rearfoot pads are applied in Varus; (2) Arch pads are applied in the Long Arch; and (3) Forefoot pads are applied behind the $2^{nd}$ through $5^{th}$ metatarsal heads in Varus.

Example 2

During examination, a patient's Rearfoot and Forefoot measurements are taken according to the present invention. The patient shows a Rearfoot SERM position as inverted, a Rearfoot PERM position as everted, a Forefoot SERM as plantarflexed and a Forefoot PERM as Dorsiflexed. Accordingly, the patient's functional foot type is Rearfoot Flexible/Forefoot Flexible. Functional Foot Type orthotics of the present invention are casted according to the following procedures: (1) the Rearfoot position technique is applied to vertical; (2) the Rearfoot Enhancement technique is applied; (3) the Forefoot Vault Enhancement technique is applied; and (4) the Hammertoe Correction technique is applied. The functional foot type orthotics of the present invention are prescribed as follows: (1) the Rearfoot is prescribed posted to Vertical; (2) the Forefoot is prescribed posted to Varus; and (3) An aggressive first ray cutout is prescribed.

What is claimed is:

1. A method for classifying foot types based on positional measurements of a human foot comprising the steps of:
   with a patient in a supine position,
   a. measuring a Rearfoot Supinatory End Range of Motion position in the foot and determining whether the position is one of inverted or everted;
   b. measuring a Rearfoot Pronatory End Range of Motion position in the foot with reference to a bisection of the lower one third of a patient's leg after applying an eversion force upon the Calcaneous until it can no longer move, and determining whether the position is one of inverted, perpendicular or everted;
   c. measuring a Forefoot Supinatory End Range of Motion position in the foot with reference to the foot's fifth metatarsal after applying a plantarflectory force downward upon the foot's first metatarsal from above until it can no longer move and determining whether the position is one of dorsiflexed or plantarflexed;
   d. measuring a Forefoot Pronatory End Range of Motion position in the foot with reference to the fifth metatarsal after applying a dorsiflectory force upward upon the first metatarsal from below until it can no longer move and determining whether the position is one of dorsiflexed, vertical or plantarflexed; and
   e. classifying the foot into a distinct foot type selected from a group of sixteen different foot types, each of said sixteen foot types being determined based on the position of the foot according to results of steps a) through d).

2. The method according to claim 1 wherein a Rearfoot in a human foot is classified based on the positional measurements of steps a) and b).

3. The method according to claim 1 wherein a Forefoot in a human foot is classified based on the positional measurements of steps c) and d).

4. A method of treating podiatric conditions in a human patient comprising the steps of:
   with a patient in a supine position,
   a. measuring a Rearfoot Supinatory End Range of Motion position in a human foot and b. measuring a Rearfoot Pronatory End Range of Motion in the foot with reference to a bisection of the lower one third of a patient's leg after applying an eversion force upon the Calcaneous until it can no longer move, and determining whether the position is one of inverted, perpendicular or everted;
   c. measuring a Forefoot Supinatory End Range of Motion position in the foot with reference to the foot's fifth metatarsal after applying a plantarflectory force downward upon the foot's first metatarsal from above until it can no longer move and determining whether the position is one of dorsiflexed or plantarflexed;
   d. measuring a Forefoot Pronatory End Range of Motion position in the foot with reference to the fifth metatarsal after applying a dorsiflector force upward upon the first metatarsal from below until it can no longer move; and determining whether the position is one of dorsiflexed, vertical or plantarflexed;
   e. classifying the foot into a distinct foot type selected from a group of sixteen different foot types, each of said sixteen foot types being determined based on the position of the foot according to results of steps a) through d); and
   f. treating the patient according to the patient's distinct foot type.

5. The method according to claim 4 wherein the treatment comprises treating a patient with pre-orthotic foot pads.

6. The method according to claim 4 wherein the treatment comprises treating a patient with orthotic inserts.

7. The method according to claim 5 wherein the pre-orthotic pads are placed onto a shoe insole or directly into a shoe.

8. A method for customizing an orthotic insert comprising measuring a patients foot type and customizing orthotic postings onto the orthotic insert based on the the patient's foot type, wherein the foot type is determined by measuring, with a patient in a supine position,
   a. a Rearfoot Supinatory End Range of Motion position in the foot and determining whether the position is one of inverted or everted;
   b. a Rearfoot Pronatory End Range of Motion position in the foot with reference to a bisection of the lower one third of a patient's leg after applying an eversion force upon the Calcaneous until it can no longer move, and determining whether the position is one of inverted, perpendicular or everted;
   c. a Forefoot Supinatory End Range of Motion position in the foot with reference to the foot's fifth metatarsal after applying a plantarflectory force downward upon the foot's first metatarsal from above until it can no longer move and determining whether the position is one of dorsiflexed or plantarflexed;
   d. a Forefoot Pronatory End Range of Motion position in the foot with reference to the fifth metatarsal after applying a dorsiflectory force upward upon the first metatarsal from below until it can no longer move and determining whether the position is one of dorsiflexed, vertical or plantarflexed; and
   classifying the foot into a distinct foot type selected from a group of sixteen different foot types, each of said sixteen foot types being determined based on the position of the foot according to results of steps a) through d).

* * * * *